United States Patent [19]

Alesandrini, Jr. et al.

[11] Patent Number: 4,551,325

[45] Date of Patent: Nov. 5, 1985

[54] METHOD FOR CONDUCTING A CHEMICAL PROCESS IN A PACKED MULTI-TUBULAR REACTOR

[75] Inventors: Carlo G. Alesandrini, Jr.; Louie A. Nady, both of Berkeley, Calif.

[73] Assignee: Stuaffer Chemical Company, Westport, Conn.

[21] Appl. No.: 549,150

[22] Filed: Nov. 7, 1983

[51] Int. Cl.⁴ .................. C01B 7/01; C07C 153/01
[52] U.S. Cl. .................. 423/488; 423/659; 422/197; 260/455 R
[58] Field of Search .............. 422/197; 423/240, 416, 423/468, 488, 659; 260/455 R; 159/47.1, 49; 202/237; 205/78, 84; 55/55, 199, 45; 204/158 H

[56] References Cited

U.S. PATENT DOCUMENTS

| | | | |
|---|---|---|---|
| 1,631,162 | 6/1927 | Sebald | 165/13 |
| 2,165,490 | 7/1939 | Kranz | 422/197 |
| 2,696,465 | 12/1954 | Kittredge | 202/185 |
| 2,878,108 | 3/1959 | Chandler | 422/197 |
| 3,230,055 | 1/1966 | Wolfrom | 422/197 |
| 3,356,125 | 12/1967 | Standiford | 159/49 |
| 3,787,188 | 1/1974 | Lyon | 422/198 |
| 3,898,058 | 8/1975 | McGill | 55/50 |
| 3,929,421 | 12/1975 | Werges | 422/193 |
| 3,997,389 | 12/1976 | Winkler | 159/49 |
| 4,119,659 | 10/1978 | Alesandrini | 260/455 R |
| 4,349,524 | 9/1982 | Yamashita et al. | 423/488 |

Primary Examiner—Howard S. Williams
Attorney, Agent, or Firm—Joel G. Ackerman

[57] ABSTRACT

A method for conducting a chemical process in which a feed containing at least one liquid is introduced into a vessel containing a plurality of packed, vertically arranged tubes, and in which at least one liquid product and at least one gaseous product are obtained, in which the tubes and a space above them are kept flooded with liquid by controlled removal of liquid product from the lower portion of the vessel.

11 Claims, 6 Drawing Figures

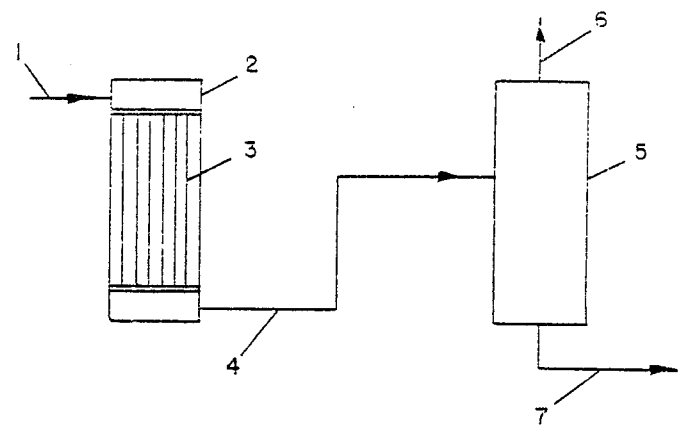
FIG. 1 (PRIOR ART.)
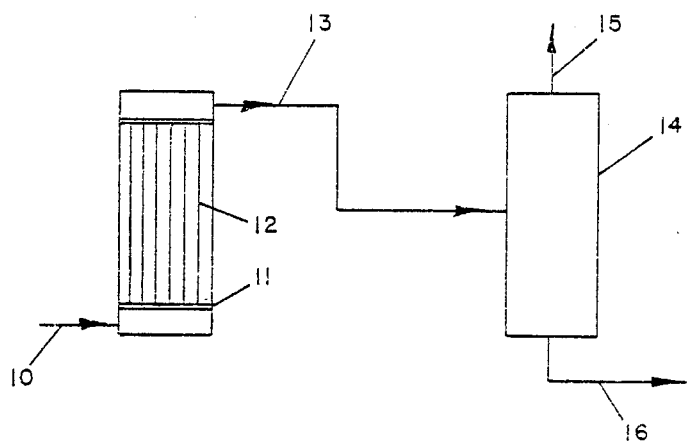
FIG. 2 (PRIOR ART.)

METHOD FOR CONDUCTING A CHEMICAL PROCESS IN A PACKED MULTI-TUBULAR REACTOR

BACKGROUND AND PRIOR ART

This invention relates to an improved method for conducting a chemical process in a multi-tubular vessel containing a plurality of packed vertically arranged tubes. In particular, this invention relates to an improvement in conducting a process in such a vessel in which a feed which contains at least one liquid is introduced into the vessel and in which at least one liquid product and at least one gaseous product are obtained. In such processes, the gaseous product may be, for instance, a gas which had been also introduced as a feed or which was dissolved in the liquid and is recovered as a vapor from the vessel, a liquid introduced as feed which becomes vaporized during the conduct of the process, or a gas produced by a chemical reaction of the liquid feed or between the liquid feed and another reactant introduced. Similarly, the liquid product obtained may be a portion of the liquid feed which, for instance, was not reacted in the vessel, or a liquid product obtained by reaction of the liquid feed with another reactant.

Examples of processes which may be generally carried out in packed multi-tubular reactors are those which are exothermic or endothermic such as hydrocarbon reforming, cyclization, dehydrogenation, desulfurization and dehydration. The packing may include one or more catalysts know to effectuate such reactions.

Generally, heat transfer to or from the tubes is accomplished through the use of gaseous or liquid heat transfer fluid in the shell space surrounding the tubes.

When operating such chemical processes in vessels containing a plurality of vertically arranged packed tubes, generally speaking, one of two methods of operation are utilized, which are illustrated in FIGS. 1 and 2.

According to FIG. 1 a liquid feed is introduced in line 1 into a vessel or reactor 2 which contains a plurality of vertically arranged packed tubes 3. The liquid feed, optionally together with other feeds, is forced to flow downwardly through the tubes and the packing contained therein, and all products, liquid and gaseous, are removed from the lower portion of vessel 2 via line 4. The liquid and gaseous products contained in line 4 are then sent for further processing. One example of such is shown in FIG. 1, in which the liquid and gaseous products in line 4 are introduced into a liquid/gas separator 5, with gaseous product being removed via line 6 and liquid product via line 7.

A second method of operation of such processes is depicted in FIG. 2. In this technique, a feed containing at least one liquid is introduced via line 10 into a vessel or reactor 11 containing a plurality of vertically arranged packed tubes 12. The feed, and products produced therefrom, are forced to flow upwardly through the tubes 12 and are removed at the upper portion of the vessel in line 13. As in FIG. 1, these products in line 13 are transmitted for further processing, for instance, passed into a liquid/gas separator 14 from which gaseous product is removed via line 15 and liquid product in line 16.

One example of a process conducted as in FIG. 2 is described in U.S. Pat. No. 3,230,055, which describes an apparatus and method for continuously contacting a gas and liquid in predetermined proportions, particularly for carrying out liquid/gas phase chemical reactions.

Another process of such type is described in U.S. Pat. No. 4,119,659, which pertains to a process for producing a series of chlorothioformate compounds by reaction of a mercaptan with phosgene.

Conducting processes by means such as described above and in FIGS. 1 and 2 possesses certain disadvantages, particularly associated with lack of uniformity of distribution (and reaction) in the various tubes of the vessel and possible lack of good heat transfer (either addition of heat to or removal of heat from the tubes).

For instance, when operating with forced downflow and removal of all products from the lower portion of the vessel as in FIG. 1, the tubes will function as miniature trickle bed reactors because of the gases produced. This results in considerably less efficient transfer of heat to or from the tubes than is desired. In addition, liquid may flow more rapidly into and down the tubes located closer to the liquid inlet or inlets then tubes located further away. In such operations, therefore, there may be a lack of uniformity of conditions from tube to tube, and a somewhat inefficient use of tubes, since some will carry more of the process load than others. Transfer of heat to or from tubes will similarly be nonuniform and thus generally less efficient. This may result in poor control of this reaction; the yield may be reduced, and/or undesired by-products may be formed.

Additionally, if the process to be conducted is one which involves a comparatively long reaction, the reactants may flow through the tubes too quickly, and reaction may not be complete.

Operation of such process according to FIG. 2, that is with introduction of liquid feed into the lower portion of the vessel and removal of liquid and gaseous products from the upper portion, can result in improved performance. Howwever, there may still be a nonuniform utilization of the tubes in the vessel. If for any reason the rate of reaction varies from tube to tube, an imbalance may occur. The tubes with the most reaction, and therefore the greatest rate of gas generation, will have the lowest pressure drop, which is dependent on the proportion of gas to liquid within each tube. More feed therefore will flow to these tubes, which then generate gas faster, and experience a temperature rise, and because of the low pressure drop, liquid will feed quicker to these tubes than to the others. The result can be that the flow rates may vary widely from tube to tube, with some tubes having very high flow rates, while others, very low ones, possibly extending to zero or negative flow rates (i.e., liquid circulates downwards rather than upwards).

In either type of process according to the prior art, nonuniform distribution and flow of materials through the tubes can result in lower than desirable conversion of liquid feed to desired product, and possibly increased production of unwanted by-products. Control of temperature and heat transfer to and from tubes becomes more difficult. Temperatures can vary from tube and affect efficiency and heat utilization of processes in general. If the reaction being conducted is temperature-sensitive, undesirable or less advantageous operational results can occur.

It is an object of the present invention to provide an improved method for operating a chemical process in a vessel or reactor containing a plurality of vertically arranged packed tubes, in which a liquid feed is introduced into the vessel, and in which at least one liquid and at least one gaseous product are obtained, which improves the performance of the process with respect to stability and uniformity of distribution of materials through the tubes and uniformity of heat transfer.

A secondary objective of this invention is to provide such an improved process for use in the production of chlorothioformates which are liquids, by reaction of a liquid mercaptan with phosgene, which may be in liquid or gaseous form, and in which gaseous products such as hydrogen chloride and optionally phosgene are obtained.

SUMMARY OF THE INVENTION

This invention comprises a method for conducting a liquid phase chemical process in which a feed containing at least one liquid is introduced into a vessel containing a plurality of packed, vertically arranged tubes, and in which at least one liquid product and at least one gaseous product are obtained, comprising:

(a) introducing the liquid feed into the vessel at a point above the upper ends of the tubes;

(b) removing a gaseous product from the upper portion of the vessel, above the upper ends of the tubes; and (c) removing a liquid product from the lower portion of the vessel in a controlled manner so as to maintain the level of liquid in the vessel above the upper ends of the tubes substantially throughout the interior of the vessel.

BRIEF DESCRIPTION OF THE DRAWINGS

Reference will be made herein to the drawings, in which:

FIG. 1 represents a general flow scheme for one prior art technique for carrying out such a process, in downflow operations;

FIG. 2 represents a second technique in the prior art for carrying out such a process, in upflow operations;

DETAILED DESCRIPTION OF THE INVENTION

Figure 3:
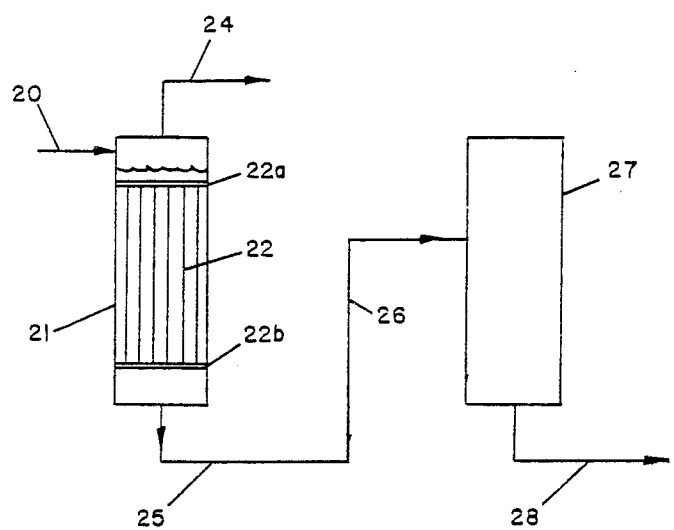
FIG. 3 schematically represents a general process carried out according to the present invention.
Figure 4:
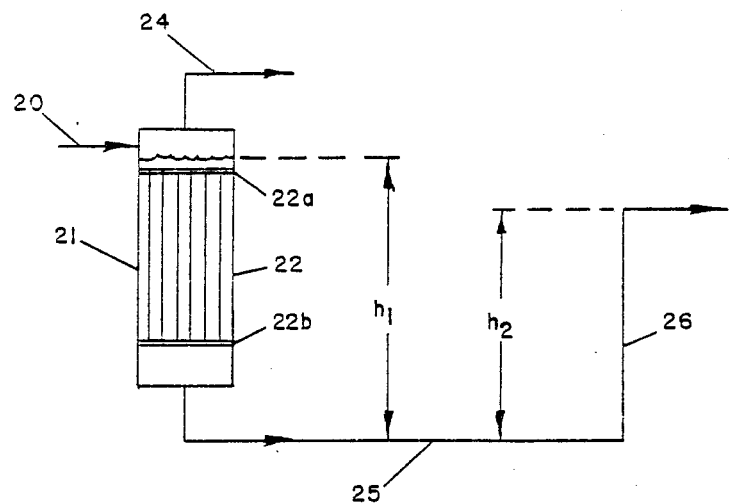
FIG. 4 schematically represents a process carried out according to one embodiment of the invention.

The conduct of processes according to the invention will be described with reference to FIGS. 3-6.

The process is carried out in a vertically situated vessel or reactor, designated generally as 21. In the upper portion of the vessel 21 is a liquid/vapor disengagement zone 23. Within the vessel are situated a plurality of vertically arranged tubes 22 which are held in place by upper and lower tube sheet 22a and 22b, respectively. The tubes are packed essentially from top to bottom with a particulate solid material. If the chemical process to be carried out is enhanced by the use of a catalyst, the particulate material may contain catalytic material, either per se, or supported on an inert particulate support. If the process to be carried out does not require the presence of a catalyst, the particulate material may be some inert material which enhances in some other way the conduct of the process, for instance a packing, an adsorbent, an absorbent, an ion exchange resin, etc.

A liquid feed, which may be a single liquid, a mixture of liquids, or a mixture of one or more liquids with one or more gases, is introduced into the upper portion of the vessel 21 via line 20, above the upper tube sheet 22a. The liquid, together with such other feeds as may be introduced, is caused to flow downwardly through the packed tubes 22. A liquid product, which may comprise an originally fed liquid, a liquid produced by a chemical reaction within the packed tubes 22, or a mixture of two or more such liquids, is withdrawn from the lower portion of the vessel, below the lower tube sheet 22b, via line 25 which includes a vertical upleg 26.

The liquid product in line 25 is passed to a downstream section 27 for further processing, such as conducting a further reaction, or separating liquid products. A final desired liquid product is obtained and withdrawn via line 28.

A gaseous product, which may be a gas originally introduced along with the liquid feed in line 20 (e.g., dissolved in the liquid), a vaporized liquid introduced through line 20, a gaseous product produced by a chemical reaction in the packed tubes 22, or a mixture of two or more of the above, is withdrawn from the upper portion of reactor 21 in line 24, and may similarly be passed downstream for further processing as desired. More preferably, the gas is withdrawn at a point above the liquid inlet or inlets.

In a preferred embodiment, the process according to the present invention is carried out continuously, with continuous introduction of a liquid feed in line 20, continuous withdrawal of a liquid product in line 25, and continuous withdrawal of a gaseous product in line 24. However, the process may also be carried out batchwise.

The conduct of the process is accomplished in the liquid phase, by maintaining the packed tubes 22 essentially uniformly filled with liquid, by causing the reactor to become flooded with liquid, while the gaseous product or products, whether originally introduced, or generated in the packed tubes, passes upwardly through the liquid and is removed as overhead from the vessel. The liquid level in the vessel is maintained above the upper ends of the tubes substantially throughout the interior of the vessel in order to keep the tubes filled with liquid.

The flooding of the tubes with liquid is accomplished by controlling the removal of liquid from the reactor in line 25 to provide a sufficient back pressure on the liquid, causing the liquid to back up and overflow through the upper ends of the tubes 22 into the space above tube sheet 22a. The same back pressure causes the gaseous product to flow upwardly through the tubes rather than cocurrently downward with the liquid, as in the prior art (Cf. FIG. I). The inlet through which the liquid is introduced in line 20 may be above or below the liquid surface in the upper portion of vessel 21. Most preferably, for best distribution, the liquid in line 20 is introduced into the vessel through a multiplicity of inlets arranged circumferentially around the upper portion of the vessel, above the upper tube sheet. The removal of the liquid in line 25 may be controlled by a number of means, including loop seals, preferably by a regulated upleg 26 on the liquid take-off line 25. Preferably the control of the liquid removal in line 25 is performed in response to signals from one or more sensing devices located in the upper portion of the vessel 21, above the upper tube sheet, which indicate the height of the liquid level in this upper portion. In one embodiment, the liquid removal in line 25 may be controlled automatically by computer process controls (not shown), in response to such signals. Regulation of the liquid in this manner can be performed by conventional flow regulators, including loop seals, valves, etc., installed in line 25.

Another means of controlling the liquid is to regulate the liquid in the upleg mentioned above at a high enough level so that the value representing the product of liquid density multiplied by liquid height in uplet 26 is equal to the value of liquid density multiplied by liquid height in tubes 22. Once this balance is adjusted for a particular reaction at steady state, the control of liquid level may be performed without the use of electrical or mechanical devices. Such operation is exemplified by FIG. 4. The densities of the liquids in the tubes 22 ($d_1$) and in line 25 ($d_2$), respectively, are measured by conventional means, or are calculated after measuring a differential pressure across a given height, the height $h_1$ of the liquid in the tubes 22 is measured, and the height $h_2$ of upleg 26 is set to balance the equation $h_1 d_1 = h_2 d_2$.

Figure 5:
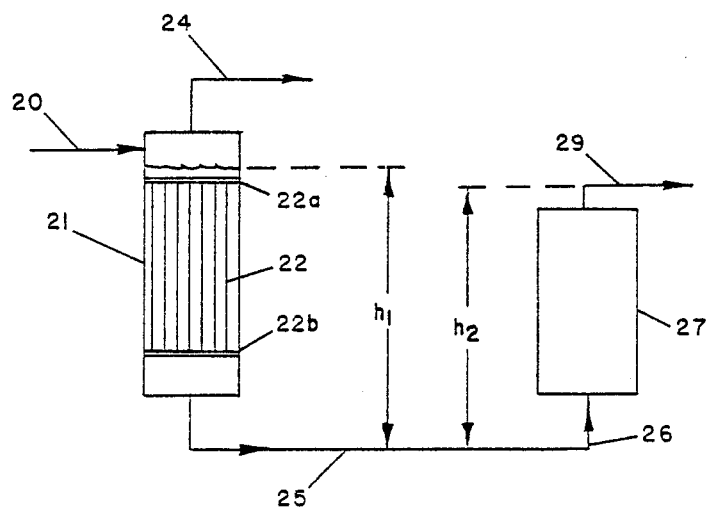
FIG. 5 schematically represents a process carried out according to another embodiment of the invention.

A similar method of operation, with downstream processing in a unit 27, is shown in FIG. 5. The overall height of liquid ($h_2$) in upleg 26, unit 27 and takeoff line 29 is determined so as to balance the equation as above.

The process may be started up by first introducing liquid into the vessel through line 20 while maintaining a controlled removal of liquid (unprocessed) in line 25 until the liquid level in the vessel is above the upper tube sheet. At this point, a reaction or other process may be commenced by, for instance, increasing the temperature within the reactor, or introducing an additional reactant into the feed.

Removing the liquid in a controlled manner as described results not only in flooding the tubes with liquid, thus maintaining uniformity of flow, but in causing the gas product to pass upwards through the tubes and out of the reactor via line 24 rather than downwardly or along with the liquid in the outlet line 25. Such control and causation of the gas flow upwards, results in a more uniform and thorough mixing of liquid and gas as well as more ready separation of the two in the vessel 21, facilitating the separate removal of liquid and gaseous products from the vessel. It further provides good heat transfer throughout the tubular zone.

Figure 6:
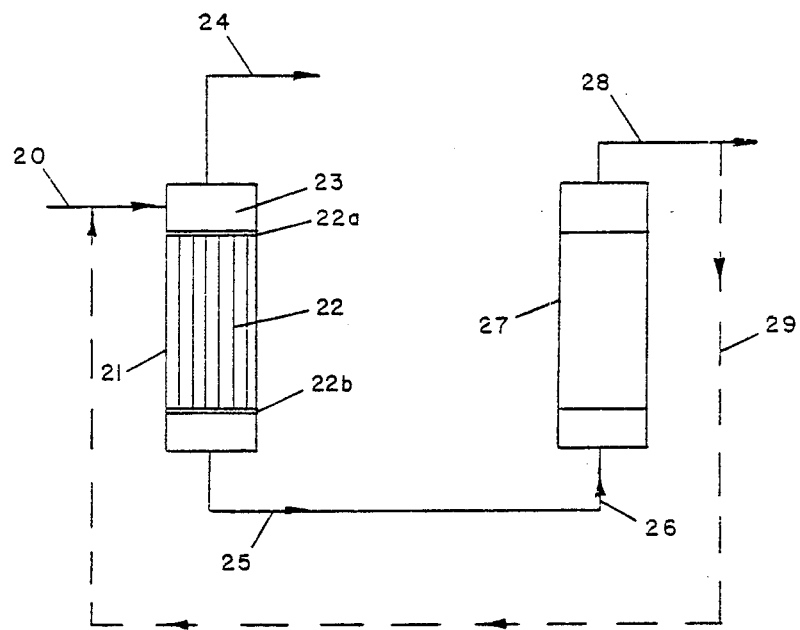
FIG. 6 represents a more detailed schematic diagram of a means for carrying out a process according to the present invention, particularly for the production of liquid chlorothioformates by reaction of a liquid mercaptan with phosgene.

For production of a liquid chlorothioformate by reaction of a liquid mercaptan with phosgene (which may be in a gaseous and/or liquid state) the process may be conducted as shown in FIG. 6.

The chloroformates desired are those having the formula a RSCOCl in which R is alkyl, lower cycloalkyl, lower cycloalkyl-methyl, lower alkenyl, phenyl, chloro-substituted phenyl, benzyl, or chloro-substituted alkyl in which the chloro substituent is situated at least as far as the gamma carbon atom, with respect to the sulfur atom. Process conditions for the production of such compounds by reaction of mercaptans with phosgene are contained in U.S. Pat. No. 4,119,659. The process will be described with reference to the production of ethyl chlorothioformate by reaction of ethyl mercaptan with phosgene, but is applicable to the production of chlorothioformates of all the general types mentioned above, utilizing the appropriate mercaptan.

A feed comprising liquid ethyl mercaptan, phosgene (preferably in the liquid state), and optionally a liquid recycle as described hereinafter, is introduced via line 20 into the upper portion of a cyclindrical reactor 21 which contains a plurality of vertically arranged tubes 22 held between an upper tube sheet 22a and a lower tube sheet 22b. The tubes 22 are packed with activated carbon catalyst of an appropriate size such that each tube functions in the conventional manner as a miniature packed bed reactor.

The liquid feed in line 20 is introduced into the upper portion 23 of reactor 21, above the upper tube sheet, preferably through a plurality of inlets arranged circumferentially around the reactor. The liquid is caused to flow downwardly through the tubes, while a pool of liquid is maintained in the upper portion of reactor 21 above the upper ends of tube 22 and the upper tube sheet 22a. In the packed tubes, mercaptan and phosgene react, resulting in the production of liquid ethyl chlorothioformate and gaseous hydrogen chloride. Additionally, some phosgene may be vaporized in the tubes. The gaseous product or products formed pass upwardly through the tubes 22, through the vapor/liquid disengagement zone 23, and are removed from the reactor in overhead line 24. These gaseous products are then passed downstream for further processing such as recovery of hydrogen chloride produced in the reaction, recovery of phosgene, and gaseous emissions control.

The reactor 21 is maintained at an average outlet temperature of generally between about 0° and about 70° C., and preferably between about 0° and about 50° C. Most preferably the temperature is between about 50° and about 65° C. at the outlet and between about 15° C. and about 40° C., at the inlet. The pressure may range between about 0 and about 150 psig, preferably between about 0 and about 50 psig, and most preferably between about 30 and about 36 psig.

A liquid product comprising primarily ethyl chlorothioformate, together with some unreacted starting materials and small amounts of by-product such as diethyl disulfide, is removed from the lower portion of reactor 21 in line 25. The rate of removal of liquid product in line 25 is controlled, for instance by a liquid level control or by passing the liquid product in line 25 through an upleg 26 which extends high enough to cause sufficient back pressure on the reactor to maintain the pool of liquid in the upper portion of reactor 21 above the upper ends of substantially all the tubes. The liquid product in line 26 is then passed to downstream apparatus 27. If the reaction in reactor 21 is not sufficiently complete, and substantial amounts of unreacted starting materials are contained in the liquid product in line 26, equipment 27 may be a second reactor for further reaction of ethyl mercaptan with phosgene, as shown in U.S. Pat. No. 4,119,659. Products are removed in line 28 and passed downstream for separation or further treatment. If, on the other hand, reaction is sufficiently complete, equipment 27 may be a separator in which the product ethyl chlorothioformate, is removed from the other materials in line 26. These other materials, comprising primarily unreacted phosgene and/or ethyl mercaptan may then be recycled in line 29 to join the liquid in line 20.

The following examples serve to illustrate the conduct of processes according to this invention.

EXAMPLE 1

(Prior Art)

A reactor system is utilized as shown in FIG. 2, having a capacity for production of about 37,000 lbs. per day of ethyl chlorothioformate. The reactor is a tubular upflow reactor, with the tubes packed with activated carbon catalyst.

Into the reactor, corresponding to reactor 11 of FIG. 2 are fed 22.4 lb.-moles/hr. of phosgene and 20.4 lb.-moles/hr. of ethyl mercaptan. The reactor is operated at an inlet temperature of about 15°–40° C., an outlet temperature of about 50°–65° C., and an outlet pressure of about 30–36 psig. Conversion of ethyl mercaptan to the chlorothioformate is about 60%. The product after removing the unreacted raw materials is produced in 98% purity, containing about 0.5–1% diethyl disulfide and about 1% diethyl dithiocarbonate.

EXAMPLE 2

A reactor is utilized as in FIG. 3, according to this invention. This reactor has the same number of tubes, is the same size and contains the same amount of carbon catalyst as the reactor in Example 1. However, the capacity of production for this reactor is about 57,000 lbs. per day of ethyl chlorothioformate. This reactor is operated in the flooded downflow mode with the tubes packed with activated carbon catalysts.

Into the reactor, corresponding to the reactor 21 of FIG. 3, are fed 22.4 lb.-moles/hr. of phosgene and 20.4 lb.-moles/hr. of ethyl mercaptan. The reactor is operated at an inlet temperature of about 15°–40° C., and an outlet temperature 50°–65° C., and an outlet pressure of about 30–36 psig.

Conversion of ethyl mercaptan to the chlorothioformate is about 90%. After removing the unreacted raw materials the product is produced in 98% purity, containing about 0.5% diethyl disulfide and less than 1% diethyl dithiocarbonate.

EXAMPLE 3

A two-reactor system is utilized as shown in FIG. 6, having a capacity for production of about 171,000 lb. per day of ethyl chlorothioformate. The first reactor is a tubular flooded downflow reactor, with the tubes packed with activated carbon catalyst. The second reactor is a packed bed reactor containing a bed of carbon catalyst and is operated as an upflow reactor. Into the first reactor, corresponding to reactor 21 are fed 67.2 lb.-moles/hr. of phosgene and 61.2 lb.-moles/hr. of ethyl mercaptan.

The reactor is operated at an inlet temperature of about 15°–40° C., an outlet temperature of about 50°–65° C., and an outlet pressure of about 30–36 psig. The products from the first reactor are fed into the lower portion of the second reactor 27 together with a recycle stream containing 32.1 lb.-moles/hr. of phosgene and 14.1 lb.-moles/hr. of ethyl chlorothioformate. The second reactor is operated in an inlet temperature of about 18°–26° C., an outlet temperature of about 33°–49° C. and an outlet pressure of about 24–28 psig.

Conversion of ethyl mercaptan to the chlorothioformate is 94%. The product is produced in 98% purity, containing about 0.5% diethyl disulfide and less than 1% diethyl dithiocarbonate.

Other processes may be suitably carried out in a similar manner; further modifications and adaptations of the process described herein may be apparent to those skilled in the art.

What is claimed is:

1. A method for conducting a liquid phase chemical process in which a feed containing at least one liquid is introduced into a vessel containing a plurality of packed, vertically arranged tubes and in which at least one liquid product and at least one gaseous product are obtained, comprising:
   (a) introducing the liquid feed into the vessel at a point above the upper ends of the tubes;
   (b) removing a gaseous product from the upper portion of the vessel above the upper ends of the tubes; and
   (c) removing a liquid product from the lower portion of the vessel in a controlled manner so as to maintain the level of liquid in the vessel above the upper ends of the tubes substantially throughout the interior of the vessel.

2. A process according to claim 1 in which the liquid product is removed in step (c) in a controlled manner in response to signals generated by a sensing device located in the upper portion of the vessel above the upper ends of the tubes, indicating the liquid level therein.

3. A process according to claim 1 in which the removal of liquid product in step (c) is controlled by passing liquid product through a vertical upleg line, with the height of said leg being determined so as to maintain the liquid level in the vessel above the upper ends of the tubes substantially throughout the interior of the vessel.

4. A process according to claim 1 in which the feed contains a mixture of liquids.

5. A process according to claim 1 in which the chemical process which is carried out is a chemical reaction, and the packing contained in the tubes is a particulate catalytic material.

6. A process according to claim 5 in which the chemical process is an exothermic chemical reaction in which undesirable by-product formation may result from poor temperature control.

7. A process according to claim 5 in which the liquid product removed in step (c) is further treated to separate said liquid product from unreacted starting material liquid, and unreacted starting material liquid is recycled to step (a).

8. A process according to claim 5 in which the liquid feed comprises a mercaptan having the formula RSH in which R is alkyl, lower cycloalkyl, lower cycloalkylmethyl, lower alkenyl, phenyl, chloro-substituted phenyl, benzyl, or chloro-substituted alkyl in which the chloro substituted is situated at least as far as the gamma carbon atom, with respect to the sulfur atom, and phosgene, and the liquid product comprises a chlorothioformate having the formula RSCOCl, in which R is defined as above.

9. A process according to claim 8 in which the gaseous product comprises hydrogen chloride.

10. A process according to claim 9 in which the gaseous product further comprises phosgene.

11. A process according to claim 8 in which liquid chlorothioformate product removed from step (c) is separated from unreacted liquid mercaptan, and the latter is recycled to step (a).

* * * * *

UNITED STATES PATENT AND TRADEMARK OFFICE
CERTIFICATE OF CORRECTION

PATENT NO. : 4,551,325

DATED : November 5, 1985

INVENTOR(S) : Carlo G. Alesadrini, Jr. et al.

It is certified that error appears in the above-identified patent and that said Letters Patent is hereby corrected as shown below:

In Column 8, Claim 8, at line 50, the word "substituted" should be --- substitutent---.

Signed and Sealed this

Thirteenth Day of January, 1987

*Attest:*

DONALD J. QUIGG

*Attesting Officer*    *Commissioner of Patents and Trademarks*